(12) United States Patent
Deckman et al.

(10) Patent No.: US 8,298,145 B2
(45) Date of Patent: Oct. 30, 2012

(54) PERI-CAPSULAR FIBROID TREATMENT

(75) Inventors: Robert K. Deckman, San Bruno, CA (US); Craig Gerbi, Half Moon Bay, CA (US); Michael Munrow, Belmont, CA (US); Jordan Bajor, Palo Alto, CA (US); Jessica Grossman, San Francisco, CA (US)

(73) Assignee: Gynesonics, Inc., Redwood City, CA (US)

( * ) Notice: Subject to any disclaimer, the term of this patent is extended or adjusted under 35 U.S.C. 154(b) by 739 days.

(21) Appl. No.: 11/775,452

(22) Filed: Jul. 10, 2007

(65) Prior Publication Data
US 2008/0033493 A1  Feb. 7, 2008

Related U.S. Application Data

(60) Provisional application No. 60/821,006, filed on Aug. 1, 2006.

(51) Int. Cl.
*A61B 8/00* (2006.01)
(52) U.S. Cl. ........................................ 600/439
(58) Field of Classification Search ........... 600/437, 600/439, 485, 488; 601/2–4; 604/19; 606/1, 606/20, 27, 32; 607/2, 80
See application file for complete search history.

(56) References Cited

U.S. PATENT DOCUMENTS

| | | | |
|---|---|---|---|
| 5,456,689 A | | 10/1995 | Kresch et al. |
| 5,607,389 A | * | 3/1997 | Edwards et al. ............. 604/22 |
| 5,908,385 A | * | 6/1999 | Chechelski et al. ......... 600/374 |
| 5,979,453 A | | 11/1999 | Savage et al. |
| 6,579,298 B1 | * | 6/2003 | Bruneau et al. ............. 606/159 |
| 6,626,855 B1 | * | 9/2003 | Weng et al. ................. 601/3 |
| 6,921,398 B2 | * | 7/2005 | Carmel et al. ............... 606/41 |
| 2005/0107781 A1 | | 5/2005 | Ostrovsky et al. |
| 2006/0189972 A1 | | 8/2006 | Grossman |
| 2007/0083082 A1 | * | 4/2007 | Kiser et al. ................ 600/115 |
| 2007/0249939 A1 | | 10/2007 | Gerbi et al. |

OTHER PUBLICATIONS

U.S. Appl. No. 11/271,151, filed Nov. 5, 2005; inventor: Jessica Grossman.
International Search Report and Written Opinion of PCT Application No. PCT/US07/74859, dated Jul. 15, 2008, 8 pages.

* cited by examiner

*Primary Examiner* — Jonathan Cwern
(74) *Attorney, Agent, or Firm* — Wilson, Sonsini, Goodrich & Rosati

(57) ABSTRACT

Uterine fibroids and other tissue masses are treated using an electrode or other treatment element introduced into a potential or peri-capsular space surrounding the fibroid under ultrasonic imaging. A therapy is delivered into the potential space by the treatment element in order to reduce or eliminate blood supply to the fibroid or other tissue mass.

28 Claims, 7 Drawing Sheets

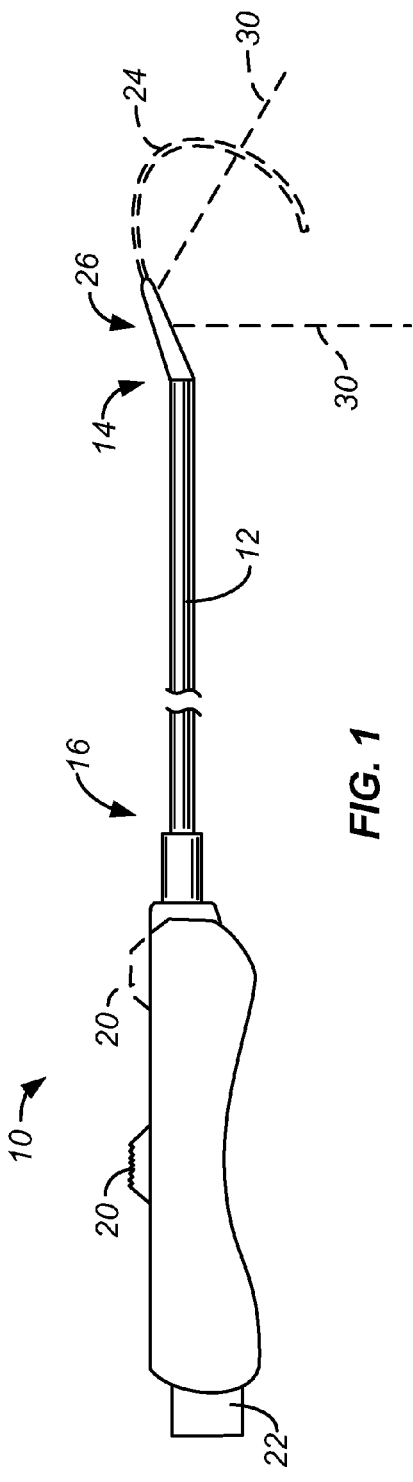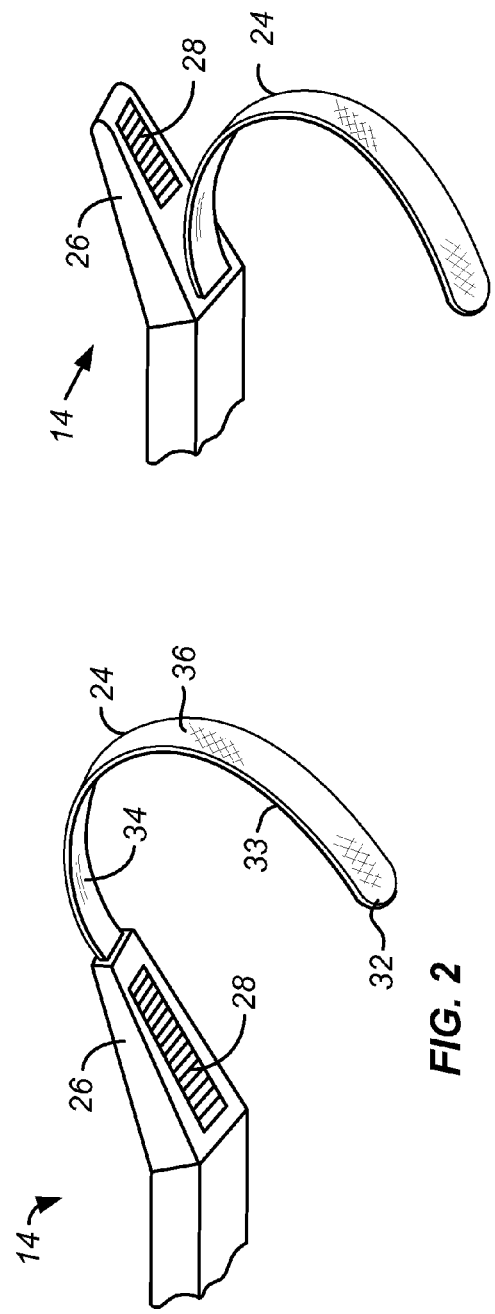
FIG. 1
FIG. 2
FIG. 3

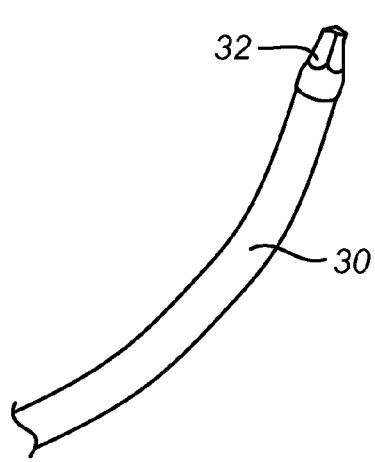
FIG. 4
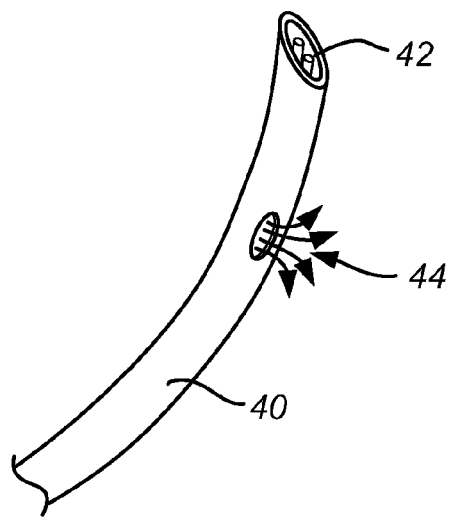
FIG. 5
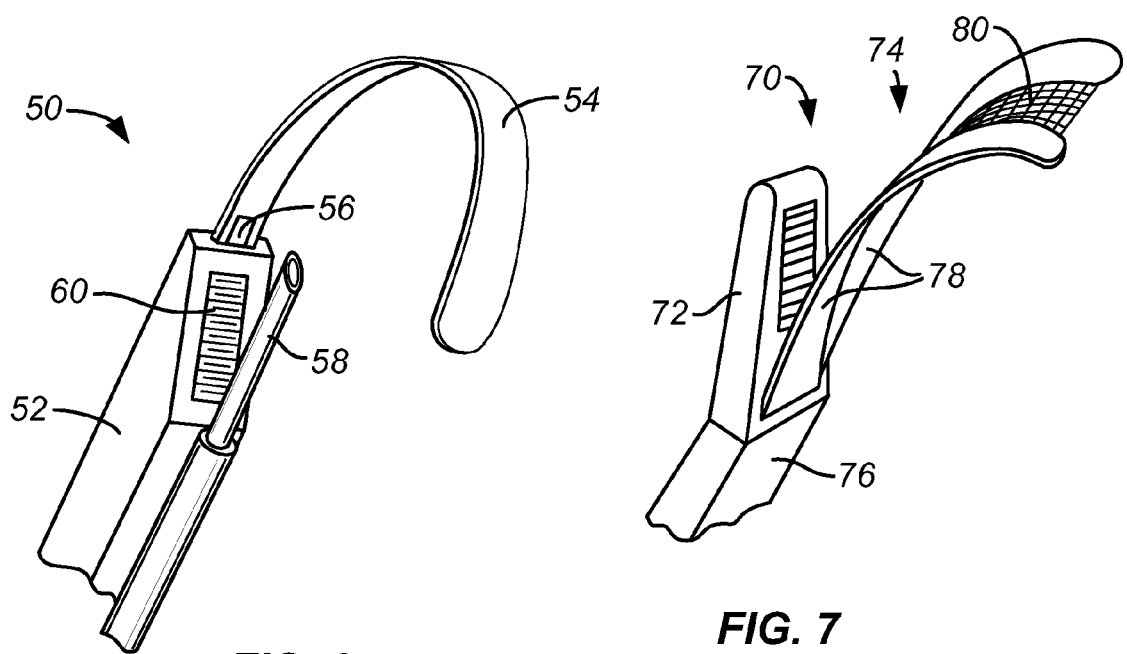
FIG. 6
FIG. 7

PERI-CAPSULAR FIBROID TREATMENT

CROSS-REFERENCES TO RELATED APPLICATIONS

The present application claims the benefit of provisional U.S. Application No. 60/821,006, filed Aug. 1, 2007, the full disclosure of which is incorporated herein by reference.

BACKGROUND OF THE INVENTION

1. Field of the Invention

The present invention relates generally to medical systems and methods. More particularly, the invention relates to methods for treating fibroids and other tissue masses in a potential space between the tissue mass and surrounding tissue.

Treatment of the female reproductive tract and other conditions of dysfunctional uterine bleeding and fibroids remain unmet clinical needs. Fibroids are benign tumors of the uterine myometria (muscle) and are the most common tumor of the female pelvis. Fibroid tumors affect up to 30% of women of childbearing age and can cause significant symptoms such as discomfort, pelvic pain, mennorhagia, pressure, anemia, compression, infertility and miscarriage. Fibroids may be located in the myometrium (intramural), adjacent to the endometrium (submucosal) or in the outer layer of the uterus (subserosal). Most commonly fibroids are a smooth muscle overgrowth that arise intramurally and can grow to be several centimeters in diameter.

Uterine fibroids are surrounded by a tissue interface referred to as a pseudo-capsule. The pseudo-capsule will usually provide a clear tissue plane between the fibroid and the surrounding tissue (myometrium), which potential space is often referred to as the peri-capsular space. At times, the fibroid may be mobile within this space.

Current treatments for fibroids include both pharmacological therapies and surgical interventions. Pharmacological treatment includes the administration of medications such as NSAIDS, estrogen-progesterone combinations, and GnRH analogues. All medications are relatively ineffective and are palliative rather than curative. Hysterectomy (surgical removal of the uterus) is another common treatment for fibroids. While effective, hysterectomy has many undesirable side effects such as loss of fertility, open surgery, sexual dysfunction and long recovery time. There is also significant morbidity (sepsis, hemorrhage, peritonitis, bowel and bladder injury), mortality and cost associated with hysterectomy. Surgical myomectomy, in which fibroids are removed, is an open surgical procedure requiring laparotomy and general anesthesia. Often these procedures are long with significant blood loss and can only remove a portion of the culprit tissue.

To overcome at least some of the problems associated with open surgical procedures, laparoscopic myomectomy was pioneered in the early 1990's. However, laparoscopic myomectomy remains technically challenging, requiring laparoscopic suturing which limits its performance to only the most skilled of laparoscopic gynecologists. Other minimally invasive treatments for uterine fibroids include hysteroscopy, uterine artery ablation, endometrial ablation, and myolysis.

Hysteroscopy is the process by which a thin fiber optic camera is used to image inside the uterus and an attachment may be used to destroy tissue. Hysteroscopic resection is a surgical technique that uses a variety of devices (loops, roller balls, bipolar electrodes) to ablate or resect uterine tissue. The uterus needs to be filled with fluid for better viewing and thus has potential side effects of fluid overload. Hysteroscopic ablation is limited by its visualization technique and is thus only appropriate for those fibroids that are submucosal and/or protrude into the uterine cavity.

Uterine artery embolization was introduced in the early 1990's and is performed through a groin incision by injecting small particles into the uterine artery to selectively block the blood supply to fibroids. Complications include pelvic infection, premature menopause and severe pelvic pain. In addition, long term MRI data suggest that incomplete fibroid infarction may result in regrowth of infarcted fibroid tissue and symptomatic recurrence.

Endometrial ablation is primarily a procedure for dysfunctional (or abnormal) uterine bleeding and may be used at times for fibroids. Endometrial ablation relies on various energy sources such as cryo energy, microwave energy and radiofrequency energy. Endometrial ablation destroys the endometrial tissue lining the uterus but does not specifically treat fibroids. This technique is also not for women who desire future childbearing. Endometrial ablation remains an excellent therapy for dysfunctional uterine bleeding but is limited in its ability to treat fibroids.

Myolysis was first performed in the 1980's using lasers or RF energy to coagulate tissue, denature proteins and necrose myometrium with laparoscopic visualization. Needle myolysis can use a laparoscopic or open surgical technique to introduce one or more needles into a uterine fibroid under endoscopic or direct visual control. The needle(s) can then be used to deliver energy, cryogenic fluids, or other treatment agents in order to coagulate a significant volume of the fibroid or other tumor to cause substantial shrinkage. Laparoscopic myolysis can be an alternative to myomectomy, as the fibroids are ablated and then undergo coagulative necrosis resulting in a dramatic decrease in size and lessening of symptoms. As with all laparoscopic techniques, myolysis treatment is limited to subserosal fibroids which can be laparoscopically visualized.

As an improvement over all of the above-described techniques, it has recently been proposed in co-pending application Ser. No. 11/409,496, assigned to the assignee of the present application, to treat uterine fibroids by penetrating a needle into the fibroid under ultrasonic imaging and delivering radiofrequency energy to the fibroid to ablate the fibroid tissue. Although this protocol has proven to be highly effective in many cases, some uterine fibroids are difficult to penetrate with needle electrodes due to fibroid tissue mobility within the myometrium where the needles will deflect from the fibroid tissue. Additionally, direct heating and ablation of the fibroid can in certain instances thermally fix the fibroid within the surrounding tissue, inhibiting the desired complete removal of the fibroid.

For these reasons it would be desirable to provide alternative methods for treating and shrinking or removing uterine fibroids and other tissue masses. It would be particularly desirable if such methods were able to treat uterine fibroids which are resistant to needle penetration or otherwise difficult to penetrate and to reduce or eliminate the chance of thermally fixing the fibroid within the surrounding uterine tissue. At least some of these objectives will be met by the inventions described below.

2. Description of the Background Art

US 2005/0107781 describes a bipolar fibroid ablation device having a first tissue penetrating array that is positioned on a remote side of the fibroid and a second non-penetrating array positioned on a near side of the fibroid. U.S. Pat. No. 5,979,453 describes a needle myolysis apparatus for directing radiofrequency current to a blood vessel supplying blood to a fibroid. U.S. Pat. No. 5,456,689 describes a device for resection of the uterine wall under ultrasound imaging.

The following commonly owned applications also relate to uterine fibroid treatment: Ser. No. 11/271,151, filed on Nov. 5, 2005; Ser. No. 11/347,018, filed Feb. 2, 2006; and Ser. No. 11/409,496, filed Apr. 20, 2006. The full disclosures of each of these copending applications are incorporated herein by reference.

BRIEF SUMMARY OF THE INVENTION

The present invention provides methods and systems for treating a tissue mass in a tissue bed, where the tissue mass is surrounding by a potential space. Such tissue masses having a surrounding potential space include uterine fibroids (where the potential space is referred to as a peri-capsular space), benign tumors, and the like. A potential space is a region between opposed surfaces of different types of tissues, such as the peri-capsular space adjacent the pseudo-capsule of a uterine fibroid tissue. The potential space can be entered by an electrode or other treatment element, where the electrode or treatment element can deliver energy and/or treatment fluids or agents under conditions selected to reduce or eliminate the blood supply to the tissue mass from the surrounding tissue within the potential space.

In a first aspect of the present invention, methods for treating a tissue mass surrounded by a potential space comprise positioning at least one treatment element in the potential space while viewing the region with ultrasonic imaging. Energy or treatment fluids or agents are then delivered through the treatment element to the potential space to reduce blood supply to the tissue mass. Preferably, the treating element will be shaped or otherwise adapted to follow or track the potential space, such as a peri-capsular space as it curves or otherwise traverses the interface between the two tissue types. Optionally, the treatment element will have an arcuate or curved profile itself and will further include a blunt tip which can follow through the peri-capsular space with minimum risk of penetrating into the uterine fibroid or other tissue mass.

Positioning of the treatment element typically comprises advancing the element from a shaft located near the tissue mass. In the case of uterine fibroids, the shaft will usually be positioned within the uterus adjacent to the fibroid tissue mass. In the specific embodiments, the treatment element is advanced while imaging the tissue in a region near the tissue mass. Imaging may comprise ultrasonic imaging, typically from a location in the uterus or other body cavity adjacent to the tissue mass. Alternatively, external imaging from the patient's skin or from another body cavity could also be performed to assist in positioning the treatment element.

While the methods and systems of the present invention are particularly useful with transvaginal and transcervical access protocols, they will also be useful with open and/or laparoscopic surgery from the serosal side of the uterus. For example, if the surgeon were performing laparoscopic or open surgery to remove sub-serosal fibroids, the physician could use systems of the present invention to remove or treat intramural fibroids in the wall of the uterus which would not otherwise be accessible to them.

A preferred treatment relies on the delivery of energy, typically electrical energy and more particularly radiofrequency electrical energy. In some instances, it will be desirable to introduce saline or other electrolytic treatment fluid into the peri-capsular or other potential space to assist in conducting the treatment current throughout the space. Optionally, the saline or other electrolytic fluid may be introduced through the treatment element itself.

Alternatively or additionally, the treatment could comprise delivery of a therapeutic agent into the potential space. The therapeutic agent will typically be a fluid, either a liquid, vapor, or combination thereof. The liquid or vapor may provide for a physical treatment of the tissue enveloping the potential space. For example, steam, heated fluid, superheated fluid, superheated air or other liquids or gases, or the like, could be delivered to heat the potential space and potentially vaporize endogenous fluids within the potential space. Thus, the blood vessels and tissues could be effectively cauterized to eliminate blood supply to the fibroid or other tissue mass. In another example, a cryogenic (cold) fluid could be introduced into the potential space in order to freeze the tissue and reduce or eliminate the blood supply to the tissue mass. In still further examples, biologically active agents could be delivered into the potential space using a liquid, gas, or combination liquid/gas carrier in order to distribute fully throughout the space. Exemplary biologically active agents include antibodies and other binding proteins which could bind to the tissue surface of the tissue mass. For example, antibodies which bind to estrogen or progesterone delivered into the potential space could inhibit growth of uterine fibroids.

Further alternatively or additionally, the treatment modality could be primarily mechanical where the treatment element is advanced through the potential space to disrupt blood supply, physically injure or necrose tissue of the tissue mass, or the like. For example, the treatment element could have a sharpened edge which can be advanced through the potential space to excise any blood vessels or connecting tissue with the surrounding tissue bed. Alternatively, the treatment element could have an edge adapted to provide for radiofrequency cutting to again excise any blood vessel or other structure between the tissue mass and surrounding tissue bed. Such physical disruption protocols could be combined with energy delivery, therapeutic agent delivery, or any of the other treatment protocols and modalities described herein.

In a second aspect, the present invention provides systems for delivering treatment to a potential space surrounding a tissue mass. Systems typically comprise a shaft, an imaging element, and a treatment element advanceable from a distal end of the shaft. The imaging element is disposed to image a field of view adjacent to a distal portion of the shaft, and the treatment element is adapted to advance within the field of view to follow a path within the potential space.

The specific construction of the system may take a variety of forms. For example, the shaft is typically rigid, but could be wholly or partly flexible and rigidizable with a separate stiffening element. The imaging element will typically be an ultrasonic array disposed to view laterally from the shaft where the treatment element is advanceable from a side of the shaft into the field of view provided by the imaging element. Alternatively, the treatment element may be advanced from a distal port on the shaft and curve backwardly into the field of view provided on the lateral imaging element. Typically, the treatment element will have a blunt end adapted to follow the surface of the tissue mass in the potential space with reduced risk of penetrating tissue in the tissue mass or the surrounding tissue, but in other embodiments, the treatment element could have a sharp tip, could have a telescoping or other complex structure, could have a pressure or other sensor, etc.

In a specific embodiment, the treatment element comprises an electrode adapted to advance along a curved or arcuate path to assist in following the curvature in the potential space. In such instances, the electrode will usually have a blunt distal end to inhibit penetration into the tissue mass. In the exemplary embodiments, the electrode is formed as a ribbon with a conductive surface along an inner radius in order to deliver energy into the tissue mass and an insulating surface along an outer radius in order to protect the surrounding tissue.

In other specific embodiments, the treatment element may comprise one or more lumens for delivering treatment agents, where the lumens terminate at one or more ports which may be disposed at the distal tip and/or along the sides of the treatment element. In still further embodiments, two or more treatment elements may be disposed on a single shaft. For example, a shaft may carry a deployable electrode and a separate needle for injecting therapeutic agents, where both the electrode and the needle are advancable within the field of view of the ultrasonic imaging array.

Still further, the treatment elements may comprise conformable electrode or other structures which can be advanced over a large region of the tissue mass. Still further, the treatment elements may comprise a first component having a sharpened distal tip to access the potential space and a second component advancable from the first component, where the second component is adapted to be advanced through the potential space, usually having a blunt distal end and being curved or otherwise conformable to the geometry of the potential space. In still further embodiments, the advancable element may comprise multiple loops, meshes, or other components which can encircle the tissue mass.

BRIEF DESCRIPTION OF THE DRAWINGS

FIGS. 1 and 2 illustrate a first exemplary apparatus for delivering energy into a peri-capsular space in accordance with the principles of the present invention.

FIG. 3 illustrates an alternative design of the distal end of the apparatus of FIGS. 1 and 2.

FIG. 4 illustrates an alternative electrode design having a circular cross-section and a blunt distal tip.

FIG. 5 illustrates an alternative treatment element design having a pressure sensor at its distal tip and a side port for delivering a therapeutic agent.

FIG. 6 illustrates a modification of the apparatus of FIG. 2 further including a saline delivery port on the electrode and a therapeutic agent delivery needle.

FIG. 7 illustrates an alternative electrode structure having two side ribbons and a conformable mesh electrode therebetween.

DETAILED DESCRIPTION OF THE INVENTION

Figure 8:
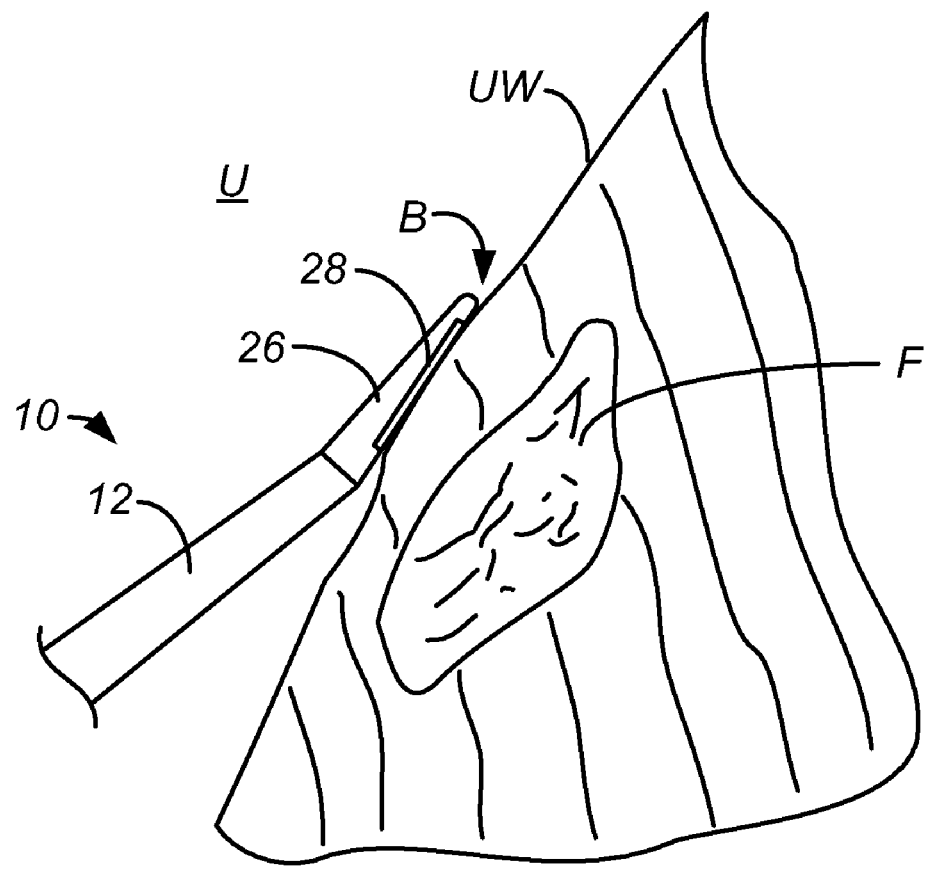
FIGS. 8 and 9 illustrate use of the apparatus of FIGS. 1 and 2 in treating a uterine fibroid in accordance with the principles of the present invention.

Referring now to FIGS. 1 and 2, an exemplary device 10 for delivering energy or other therapeutic agents into a peri-capsular or other potential space surrounding a tissue mass, such as a uterine fibroid, comprises a shaft 12 having a distal end 14 and a proximal end 16. Handle 18 is attached to the proximal end 16 and includes an axially translatable slide 20 and a power connector 22. An energy delivering or other treatment element 24 is advanceable from a distal tip of the device when the slide 20 is forwardly advanced, as shown in broken line in FIG. 1. An ultrasonic imaging assembly 26 is also provided at the distal end 14 of the shaft 12.

Referring now in particular to FIG. 2, the ultrasonic imaging assembly 26 includes an ultrasonic imaging array 28 which is adapted to image within the field of view defined by broken lines 30 in FIG. 1. The treatment element 24 is disposed to be advanced into this field of view, as also shown in FIG. 1. The treatment element 24 is preferably a ribbon-like electrode having a generally blunt or rounded tip 32 with an electrically conductive side 34 on its inner radius, an electrically insulating side 36 on its outer radius. The electrically conductive side 34 is connectable to external power through the power connector 22 by internal conductors (not shown). Alternatively, the treatment element 24 could have a sharpened and/or RF cutting enhanced side edge 33 to permit the device 10 to be rotated to sever blood vessels and other tissue structures surrounding a tissue mass.

As shown in FIG. 2, the treatment element 24 advances from the distal tip of the device 10. As shown in FIG. 3, the treatment element 24 could also be disposed to advance from a location on shaft 12 proximal to the array 28 so that it would be within the field of view 30 (FIG. 1) at an earlier portion of its travel.

As shown in FIG. 4, electrode treatment element 30 may have a circular cross-section and terminate at its distal end in a tapered tip 32 in order to facilitate advancement through a peri-capsular or other potential space between a tissue mass and a surrounding tissue bed. Although shown as a solid structure, the treatment element 30 could be provided with one or more lumens for delivering saline, therapeutic agents, or the like.

As shown in FIG. 5, a treatment element 40 intended for delivering therapeutic agents may have a pressure transducer 42 at or near its distal end. The pressure transducer will detect a drop or change in pressure as the treatment element 40 is advanced into a peri-capsular or other potential space. Once entry into the potential space is confirmed, the treatment element 40 may be advanced further until therapeutic agent delivery port 44 is within the potential space. At that time, cryogenic, biologically active, or other treatment agents may be delivered into the potential space for treatment.

Referring now to FIG. 6, a treatment device 50 can terminate in a distal imaging assembly 52 as generally described above. An electrode or other treatment element 54 may be disposed to emerge from the distal tip of the device 50, as generally described above in connection with FIG. 2. When the treatment element 54 is an electrode, a saline diffusion port 56 may be provided at the base of the treatment element or elsewhere. Optionally, a separate telescoping needle 58 may be provided for delivering therapeutic agents directly into the fibroid or other tissue mass. Both the electrode or other treatment element 54 and the needle 58 will be within the field of view of the ultrasonic imaging array 60.

Referring now to FIG. 7, a treatment device 70 may comprise a distal ultrasonic imaging assembly 72 as generally described with respect to the previous embodiments. An electrode treatment assembly 74 is mounted to emerge from a point on the shaft 76 proximal of the imaging assembly 72. The electrode treatment assembly comprises a pair of diverging ribbon-like electrodes 78 having a compliant electrically conductive mesh 80, such as a metalicized mesh, therebetween. The electrode assembly 74 may thus be atraumatically introduced into the potential space by advancing the ribbon-like electrodes 78. As the ribbon-like electrodes 78 enter the potential space, they will diverge and conform the mesh electrode 80 directly against the fibroid or other tissue mass.

Figure 9:
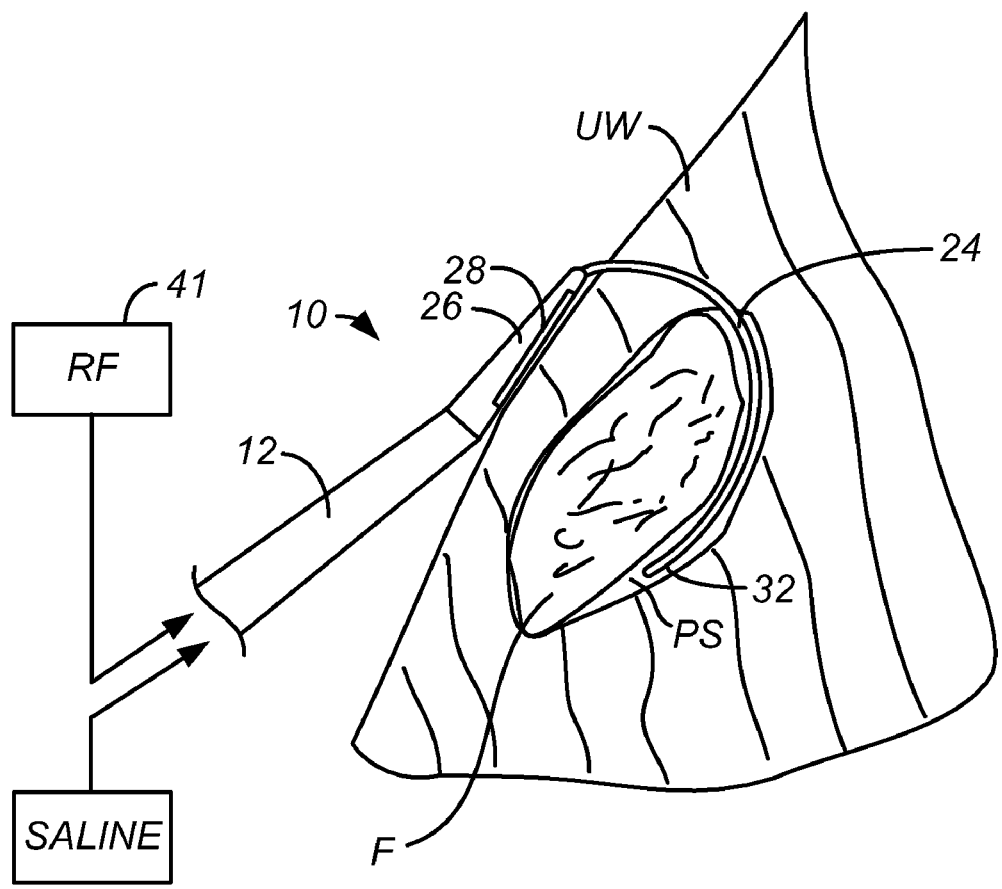

Referring now to FIGS. 8 and 9, use of the device 10 for treating a uterine fibroid F will be described. The shaft 12 is transvaginally advanced through the cervix and into the uterine cavity U, and the ultrasonic imaging element 28 utilized to locate the fibroid F. The device can be manipulated to locate the periphery of the fibroid, and then positioned so that the distal tip is adjacent a boundary B between the fibroid and the surrounding tissue. The treatment electrode 24 is then advanced by manually pushing the slide 20 forwardly so that the blunt end 32 of the element 24 enters the peri-capsular space between the fibroid and the surrounding tissue, as shown in FIG. 9. Advancement of the electrode element 24 can be observed using the imaging array 28 on the device.

Once in place, radiofrequency energy can be applied from an RF power supply 41 to deliver energy into the peri-capsular space PS. Optionally, saline or other electrolyte can be introduced through the device. If saline is to be introduced into the device, the electrode element 24 will typically be provided with small lumens and passages for delivering the saline into the peri-capsular space (not shown). Treatment will be carried out for time sufficient to reduce or eliminate the blood supply from the surrounding tissue into the fibroid.

Figure 10:
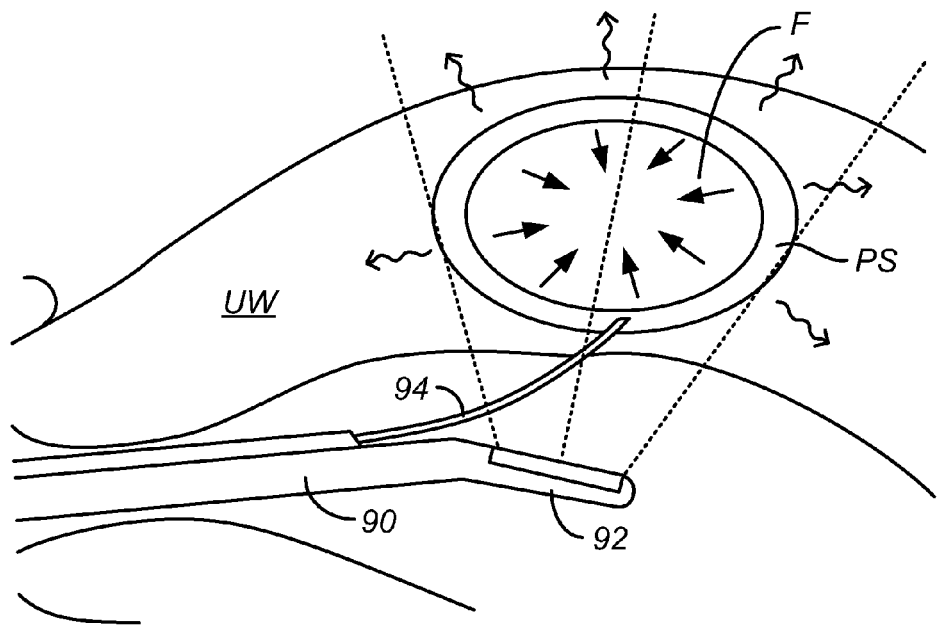
FIG. 10 illustrates a needle which is deployable to deliver a vapor or steam fluid to the potential space.

Referring now to FIG. 10, a treatment device 90 having an ultrasonic imaging assembly 92 at its distal end may be used to deploy a sharp-tipped needle 94 into a peri-capsular space PS surrounding a fibroid F. The needle may be used to deliver a variety of therapeutic or other substances. For example, the needle may be used to deliver saline or other electrolytic fluid into the peri-capsular space, with the needle thereafter used to deliver radiofrequency or other electrical treatment current to the space. The delivery of radiofrequency current into the saline will heat the saline to act as a "virtual" electrode surrounding and conforming to the fibroid for a substantially even delivery of heat. The needle treatment element 94 could also be used to deliver cryogenic fluids for cooling treatment, and/or fluids carrying antibodies and other biological treatment agents.

Figure 11:
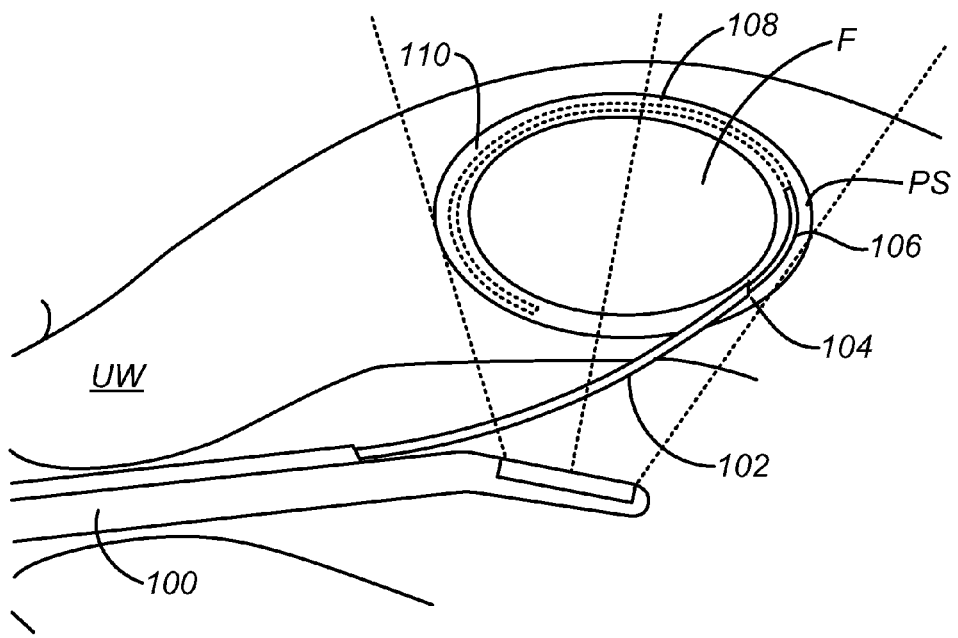
FIG. 11 illustrates a needle intended to deliver a coaxial treatment element into the potential space.

Referring now to FIG. 11, the treatment device 100 can be constructed similarly to devices 10 and 90 described previously, where the treatment element comprises a first needle structure 102 having a sharpened distal tip 104 for accessing the peri-capsular space PS surrounding a fibroid F. The first needle structure can be used to deliver any of the energy and/or therapeutic agents described previously. In addition, the needle structure 102 can be used to advance a curved, resilient electrode structure 106, typically formed from nickel titanium alloy. The electrode structure 106 can be distally advanced through regions 108 and 110 as shown in broken line in the illustration. Electrode structure 106 can be used to deliver radiofrequency or other treatment current. Additionally, the electrode structure 106 could itself have one or more fluid delivery lumens in order to deliver any of the therapeutic or other treatment agents described herein.

Figure 12:
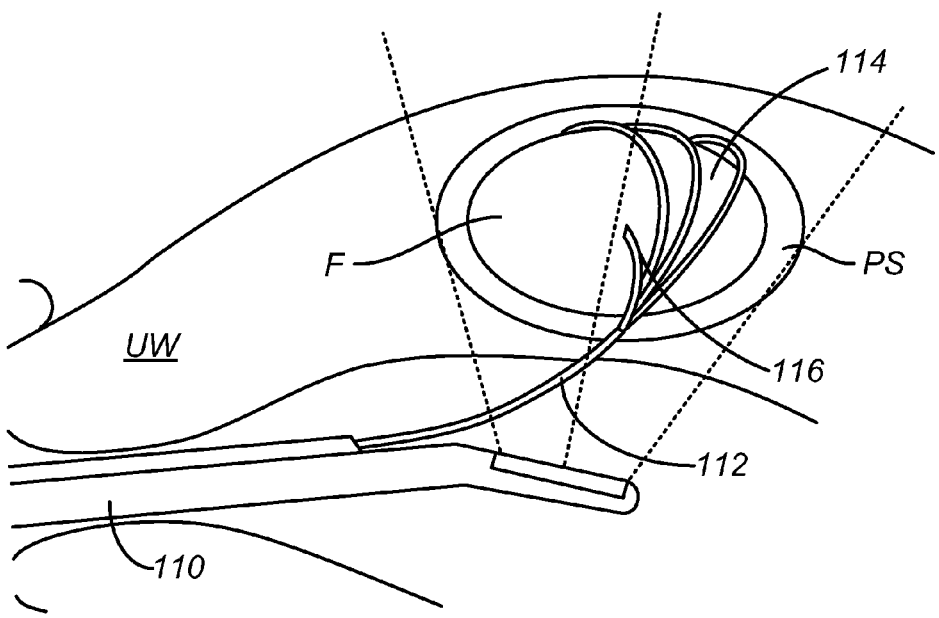
FIG. 12 illustrates a needle intended to deliver a plurality of secondary treatment elements into the potential space.

Referring now to FIG. 12, treatment device 110 has a shaft generally constructed as shown in previous FIGS. 1, 10, and 11. A first needle structure 112 can be advanced from the device 110 under direct ultrasonic observation, again as described in all prior embodiments. First needle structure 112 can itself be a needle, or alternatively may only be used to advance various secondary treatment elements into the peri-capsular space PS surrounding fibroid F in the uterine wall UW. The secondary structures may comprise, for example, a plurality of separate, distinct needle penetration elements for advancement into the peri-capsular space PS. As shown, three needle penetration elements 114 are fully advanced and surround most of the circumferential space over the fibroid F. A fourth needle penetration element 116 is in the process of being advanced around the fibroid F. Further secondary needle structures may also be provided and advanced.

Figure 13:
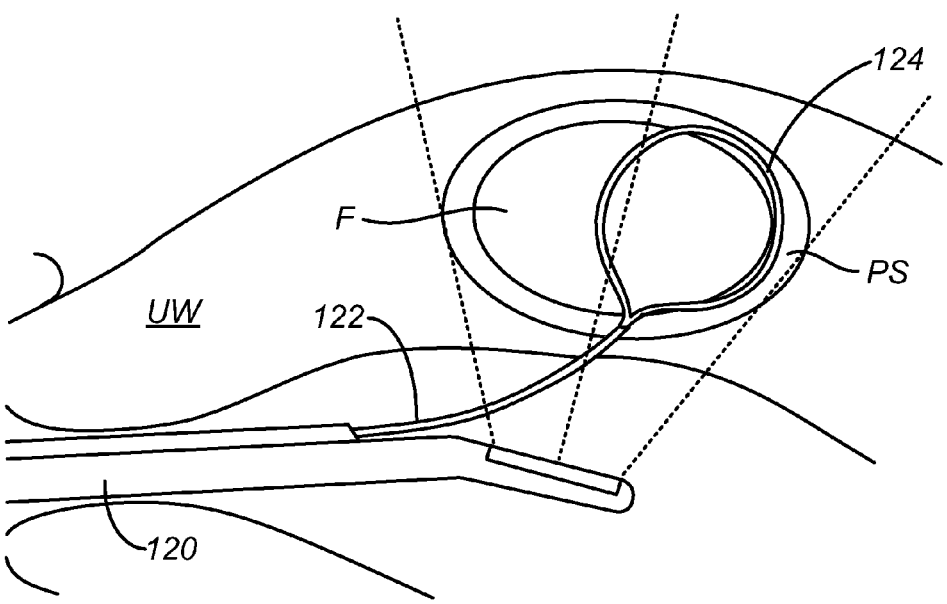
FIG. 13 illustrates a needle intended to deliver a loop treatment element into the potential space.

Referring now to FIG. 13, a treatment device 120 may have a primary needle element 122 which is used to deploy an electrode loop 124 around a fibroid F in a peri-capsular space PS.

Figure 14:
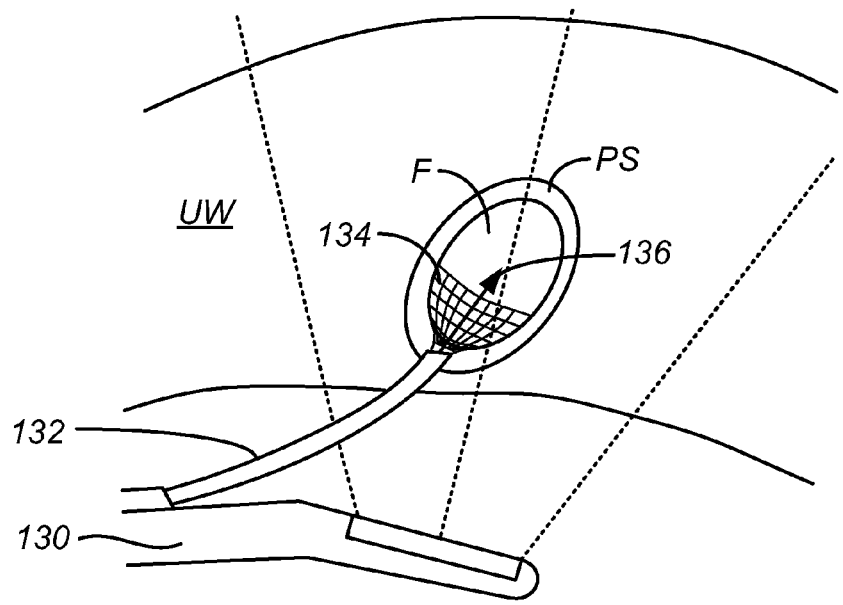
FIGS. 14 and 15 illustrate deployment of a mesh-like treatment element which can envelop the tissue mass.
Figure 15:
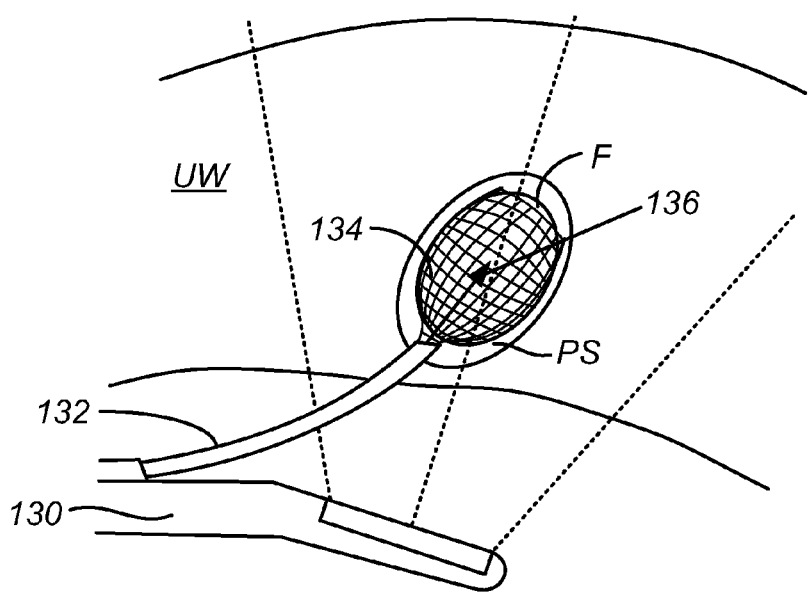

Finally, referring to FIGS. 14 and 15, a treatment device 130 has a primary needle element 132 for advancing a mesh-like electrode structure 134 in a direction 136 over a fibroid F in a peri-capsular space PS. The initial advancement is shown in FIG. 14 and a substantially complete advancement is shown in FIG. 15.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for treating a tissue mass in a tissue bed, wherein the tissue mass is surrounded by a potential space which lies between the tissue mass and the tissue bed, said method comprising:

penetrating at least one energy delivery element through the tissue bed to position a distal end of the element in the potential space, wherein said penetrating is performed under ultrasonic visualization and wherein said element does not penetrate into said tissue mass;

delivering a therapy through said element into the potential space to reduce blood supply to the tissue mass.

2. A method as in claim 1, wherein the tissue mass is selected from the group consisting of fibroids and benign tumors.

3. A method as in claim 2, wherein the tissue mass comprises a uterine fibroid and the tissue bed comprises a uterine wall.

4. A method as in claim 1, wherein positioning the element comprises advancing the element from a shaft through the tissue bed and into the potential space, wherein the element is advanced through the potential space without entering the tissue mass or reentering the tissue bed.

5. A method as in claim 1, wherein the tissue mass is a uterine fibroid surrounded by a peri-capsular space present in a uterine wall and the shaft is located in a uterus.

6. A method as in claim 1, further comprising ultrasonically imaging the tissue mass while the at least one element is being positioned.

7. A method as in claim 1, wherein the tissue mass is a uterine fibroid and imaging is carried out from a location in a uterus.

8. A method as in claim 1, wherein the therapy comprises delivering energy selected from the group consisting of electrical energy, thermal energy, and mechanical energy.

9. A method as in claim 8, wherein the energy comprises electrical energy.

10. A method as in claim 9, further comprising injecting an electrolytic fluid into the potential space before or during delivering the electrical energy.

11. A method as in claim 9, wherein the therapy comprises delivering a therapeutic agent into the potential space without penetrating said tissue mass.

12. A method as in claim 11, wherein the therapeutic agent comprises a heated fluid.

13. A method as in claim 11, wherein the therapeutic agent comprises a cryogenic fluid.

14. A system as in claim 9, wherein the electrical energy comprises RF.

15. A method as in claim 8, wherein the energy delivery comprises delivering a substance selected from the group consisting of liquid, vapor and gas.

16. A system for delivering energy to a potential space surrounding a tissue mass present in a tissue bed, said system comprising:

a shaft;

an ultrasonic imaging transducer disposed to image a field of view adjacent a distal portion of the shaft; and a treatment element advanceable from a distal end of the shaft, wherein the element is adapted to enter and follow a path in the potential space, wherein the treatment element comprises a curved ribbon having a blunt end with a conductive surface along an inner radius and an insulating surface along an outer radius.

17. A system as in claim 16, wherein the shaft is rigid.

18. A system as in claim 17, wherein the ultrasonic transducer is disposed to view laterally from the shaft and the element is advanceable into a field of view provided by the ultrasonic imaging transducer.

19. A system as in claim 18, wherein the treatment element advances from a distal port on the shaft and curves into the field of view of the imaging element.

20. A system as in claim 19, wherein the blunt end is adapted to follow the outer surface of the tissue mass in the potential space.

21. A system as in claim 16, wherein the treatment element comprises an electrode for delivering electrical energy.

22. A system as in claim 21, wherein the electrical energy comprises RF.

23. A system as in claim 16, wherein the treatment element comprises a lumen for delivering a therapeutic agent.

24. A system as in claim 16, wherein the treatment element has a sharpened edge for excising blood vessels surrounding the tissue mass.

25. A system as in claim 16, wherein the treatment element is configured to advance along a curved path to help follow the curvature of the potential space.

26. A system as in claim 16, wherein the treatment element further comprises a pressure transducer near a distal tip.

27. A system as in claim 26, wherein the treatment element further comprises a fluid infusion port located to release fluid into the potential space when the pressure transducer is within the potential space.

28. A system as in claim 16, wherein the treatment element comprises an electrode for delivering one of liquid, vapor and steam.

* * * * *